(12) United States Patent
Ryu et al.

(10) Patent No.: US 10,127,655 B2
(45) Date of Patent: Nov. 13, 2018

(54) MEDICAL IMAGING APPARATUS AND METHOD OF OPERATING SAME

(71) Applicant: Samsung Medison Co., Ltd., Hongcheon-gun (KR)

(72) Inventors: Ji-won Ryu, Seoul (KR); Jae-il Kim, Suwon-si (KR); Won-chul Bang, Seongnam-si (KR); Young-taek Oh, Hanam-si (KR); Kyong-joon Lee, Seongnam-si (KR); Jung-woo Chang, Seoul (KR); Ja-yeon Jeong, Seongnam-si (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 49 days.

(21) Appl. No.: 15/169,889

(22) Filed: Jun. 1, 2016

(65) Prior Publication Data

US 2017/0011509 A1 Jan. 12, 2017

(30) Foreign Application Priority Data

Jul. 9, 2015 (KR) .................. 10-2015-0097768

(51) Int. Cl.
*G06K 9/00* (2006.01)
*G06T 7/00* (2017.01)
(Continued)

(52) U.S. Cl.
CPC ............ *G06T 7/0012* (2013.01); *A61B 6/463* (2013.01); *A61B 6/467* (2013.01); *A61B 6/486* (2013.01);
(Continued)

(58) Field of Classification Search
CPC .......... G06T 7/0012; G06T 7/70; G06T 7/20; G06T 7/30; G06T 7/33; G06T 7/35;
(Continued)

(56) References Cited

U.S. PATENT DOCUMENTS 7,616,799 B2 11/2009 Ramamurthy et al.
8,879,814 B2 * 11/2014 Wollenweber ......... A61B 6/032
382/131

(Continued)

FOREIGN PATENT DOCUMENTS

JP 2003-144412 A 5/2003
JP 2006-217939 A 8/2006
JP 2009-247739 A 10/2009

OTHER PUBLICATIONS

Communication dated Nov. 30, 2016 issued by the European Patent Office in counterpart European Patent Application No. 16175022.9.

*Primary Examiner* — Jose Couso
(74) *Attorney, Agent, or Firm* — Sughrue Mion, PLLC

(57) ABSTRACT

Provided is a method of operating a medical imaging apparatus, comprising: acquiring a first image of a first type corresponding to a first respiratory state of an object; determining motion information of the object with respect to a respiratory state, based on first and second images of a second type respectively corresponding to the first respiratory state and a second respiratory state of the object; and generating a second image of the first type corresponding to the second respiratory state by applying the motion information to the first image of the first type.

23 Claims, 18 Drawing Sheets

(51) Int. Cl.
*A61B 6/00* (2006.01)
*A61B 8/00* (2006.01)
*A61B 8/08* (2006.01)
*G06K 9/62* (2006.01)
*G06T 7/20* (2017.01)
*G06T 11/60* (2006.01)
*G06T 7/70* (2017.01)

(52) U.S. Cl.
CPC .............. *A61B 6/50* (2013.01); *A61B 6/5235* (2013.01); *A61B 6/5247* (2013.01); *A61B 6/5264* (2013.01); *A61B 8/463* (2013.01); *A61B 8/467* (2013.01); *A61B 8/5246* (2013.01); *A61B 8/5261* (2013.01); *A61B 8/5276* (2013.01); *G06K 9/6215* (2013.01); *G06T 7/20* (2013.01); *G06T 7/70* (2017.01); *G06T 11/60* (2013.01); *G06T 2207/10081* (2013.01); *G06T 2207/20221* (2013.01); *G06T 2207/30004* (2013.01)

(58) Field of Classification Search
CPC ..................... G06T 7/38; G06T 3/4061; G06T 2207/10072; G06T 2207/10081; G06T 2207/10116; G06T 2211/40; G06T 2207/10132; G06T 2207/20221; G06T 2207/30016; G06T 2207/30061; G06T 11/003; G06T 11/005; G06T 11/008; G06T 2207/10084; G06T 2207/10088; G06T 2207/10101; G06T 2207/10104; G06T 2207/10108; G06T 2207/10121; G06T 2207/10124; G06K 9/0057; G06K 9/6215; G06K 9/03; Y10S 128/922; Y10S 378/901; A61B 6/463; A61B 6/486; A61B 6/50; A61B 6/5235; A61B 6/5247; A61B 6/5264; A61B 6/022; A61B 6/032; A61B 6/037; A61B 6/4417; A61B 5/0402; A61B 5/055; A61B 8/463; A61B 8/483; A61B 8/08; A61B 8/085; A61B 8/467; A61B 8/5246; A61B 8/5261; A61B 8/5276; A61B 8/4416; A61B 2090/3995; A61N 5/1039; A61N 5/1045; A61N 5/1067; A61N 5/107; A61N 5/1077; A61N 5/51081

See application file for complete search history.

(56) References Cited

U.S. PATENT DOCUMENTS

| | | | | |
|---|---|---|---|---|
| 9,087,397 | B2* | 7/2015 | Hwang | .................... G06T 17/00 |
| 9,582,906 | B2* | 2/2017 | Ra | ........................... G06T 11/005 |
| 2003/0216631 | A1 | 11/2003 | Bloch et al. | |
| 2008/0107312 | A1 | 5/2008 | Von Berg | |
| 2010/0145197 | A1 | 6/2010 | Stapf et al. | |
| 2012/0035462 | A1 | 2/2012 | Maurer, Jr. et al. | |
| 2013/0345545 | A1* | 12/2013 | Gross | ..................... A61B 5/055 600/411 |
| 2016/0140716 | A1* | 5/2016 | Kadir | .................... G06T 7/0028 382/131 |
| 2016/0310761 | A1* | 10/2016 | Li | ......................... A61N 5/1038 |
| 2017/0065832 | A1* | 3/2017 | Berlinger | ............. A61N 5/1049 |
| 2017/0079608 | A1* | 3/2017 | Hamill | ................. A61B 6/5235 |

* cited by examiner

670

680

MEDICAL IMAGING APPARATUS AND METHOD OF OPERATING SAME

CROSS-REFERENCE TO RELATED APPLICATION

This application claims the benefit of Korean Patent Application No. 10-2015-0097768, filed on Jul. 9, 2015, in the Korean Intellectual Property Office, the disclosure of which is incorporated herein in its entirety by reference.

BACKGROUND

1. Field

The present disclosure relates to medical imaging apparatuses and methods of operating the same, and more particularly, to medical imaging apparatuses and operation methods for matching a plurality of images.

2. Description of the Related Art

Medical imaging apparatuses are used to acquire images showing an internal structure of an object. The medical imaging apparatuses are non-invasive examination devices that capture and process images of details of structures, tissues, flow of fluids, etc., inside a body and provide the images to a user. A user, e.g., a medical practitioner, may use medical images output from the medical imaging apparatuses to diagnose a patient's condition and diseases. Examples of an apparatus for capturing and processing a medical image may include a magnetic resonance imaging (MRI) apparatus, a computed tomography (CT) apparatus, an optical coherence tomography (OCT) apparatus, a single photon emission computed tomography (SPECT) apparatus, a positron emission tomography (PET) apparatus, an X-ray apparatus, an ultrasound apparatus, etc. A medical image processing apparatus generates a medical image by processing captured image data.

Among medical imaging apparatuses, ultrasound diagnosis apparatuses transmit ultrasound signals generated by transducers of a probe to an object and receive echo signals reflected from the object, thereby obtaining an image of an internal part of the object. In particular, ultrasound diagnosis apparatuses are used for medical purposes including observing an internal area of an object, detecting foreign substances, and assessing injuries. Such ultrasound diagnosis apparatuses provide high stability, display images in real time, and are safe due to there being no radiation exposure, compared to X-ray apparatuses. Therefore, an ultrasound diagnosis apparatus is widely used together with other types of imaging diagnosis devices.

SUMMARY

Provided are medical imaging apparatuses and methods of operating the same whereby an accurate internal structure of an object is provided by matching different types of images.

Provided are medical imaging apparatuses adapted to provide a more accurate image than a single image and a matched image of the related art by matching images of different modalities in consideration of a respiratory state of an object.

Provided are non-transitory computer-readable recording media having recorded thereon a program for executing a method of operating a medical imaging apparatus on a computer.

Additional aspects will be set forth in part in the description which follows and, in part, will be apparent from the description, or may be learned by practice of the presented exemplary embodiments.

According to an aspect of an exemplary embodiment, a method of operating a medical imaging apparatus includes: acquiring a first image of a first type corresponding to a first respiratory state of an object; determining motion information of the object with respect to a respiratory state, based on first and second images of a second type respectively corresponding to the first respiratory state and a second respiratory state of the object; and generating a second image of the first type corresponding to the second respiratory state by applying the motion information to the first image of the first type.

The method may further include matching at least one of the first and second images of the first type with at least one of the first and second images of the second type.

The matching of the at least one of the first and second images of the first type with the at least one of the first and second images of the second type may include matching at least two images of the first and second types corresponding to a same respiratory state.

The method may further include displaying a matched image.

The method may further include: displaying at least one of the first and second images of the first type and at least one of the first and second images of the second type; and receiving a user input for selecting the at least one of the first and second images of the first type and the at least one of the first and second images of the second type.

The method may further include matching the selected at least one image of the first type with the selected at least one image of the second type.

The displaying of the at least one of the first and second images of the first type and the at least one of the first and second images of the second type may include at least one of: displaying the first and second images of the first type and the first and second images of the second type; and displaying at least two of the first and second images of the first type and the first and second images of the second type in such a manner that the at least two images overlap each other.

The displaying of the at least two of the first and second images of the first type and the first and second images of the second type in the overlapping manner may include at least one of: displaying the first and second images of the first type in the overlapping manner; and displaying the first and second images of the second type in the overlapping manner.

The determining of the motion information of the object with respect to the respiratory state may include: acquiring the first and second images of the second type; determining at least one parameter for acquiring motion information indicating a spatial transformation between the first and second images of the second type; determining a value of the at least one parameter based on the spatial transformation therebetween; and determining the motion information based on the determined value of the at least one parameter.

The spatial transformation may be based on at least one of a position, rotation, and a size of the object.

The determining of the motion information of the object with respect to the respiratory state may include acquiring position information of the object and determining the motion information from the first and second images of the second type respectively acquired in the first and second respiratory states corresponding to the acquired position information.

The first and second images of the first type may be computed tomography (CT) images, and the first and second images of the second type may be ultrasound images. The first and second respiratory states may be inspiratory and expiratory states of the object, respectively.

According to an aspect of an exemplary embodiment, a medical imaging apparatus includes: an image processor configured to acquire a first image of a first type corresponding to a first respiratory state of an object; and a controller configured to determine motion information of the object with respect to a respiratory state based on first and second images of a second type respectively corresponding to the first respiratory state and a second respiratory state of the object and to generate a second image of the first type corresponding to the second respiratory state by applying the motion information to the first image of the first type.

The controller may match at least one of the first and second images of the first type with at least one of the first and second images of the second type.

The controller may match at least two images of the first and second types corresponding to a same respiratory state.

The medical imaging apparatus may further include: a display configured to display at least one of the first and second images of the first type and at least one of the first and second images of the second type; and a user interface configured to receive a user input for selecting the at least one of the first and second images of the first type and the at least one of the first and second images of the second type.

The display may display at least two of the first and second images of the first type and the first and second images of the second type in such a manner that the at least two images overlap each other.

The image processor may acquire the first and second images of the second type, and the controller may determine at least one parameter for acquiring motion information indicating a spatial transformation between the first and second images of the second type, determine a value of the at least one parameter based on the spatial transformation therebetween, and determine the motion information based on the determined value of the at least one parameter.

According to an aspect of an exemplary embodiment, a non-transitory computer-readable recording medium has recorded thereon a program for performing a method of operating a medical imaging apparatus, wherein the method includes: acquiring a first image of a first type corresponding to a first respiratory state of an object; determining motion information of the object with respect to a respiratory state, based on first and second images of a second type respectively corresponding to the first respiratory state and a second respiratory state of the object; and generating a second image of the first type corresponding to the second respiratory state by applying the motion information to the first image of the first type.

According to an aspect of an exemplary embodiment, a method of operating a medical imaging apparatus includes: acquiring a first image of a first type corresponding to a first respiratory state of an object and images of a second type respectively corresponding to a plurality of respiratory states; acquiring position information of the object; determining motion information of the object with respect to a respiratory state, based on the acquired position information of the object and the images of the second type; and generating a second image of the first type corresponding to a second respiratory state by applying the motion information to the first image of the first type.

The method may further include: matching at least one of the first and second images of the first type with at least one of the images of the second type; and displaying a matched image.

The determining of the motion information with respect to the respiratory state may include determining the motion information based on the position information of the object and anatomical structures in the images of the second type.

According to an aspect of an exemplary embodiment, a medical imaging apparatus includes: an image processor configured to acquire a first image of a first type corresponding to a first respiratory state of an object and images of a second type respectively corresponding to a plurality of respiratory states; and a controller configured to acquire position information of the object, determine motion information of the object with respect to a respiratory state, based on the acquired position information of the object and the images of the second type, and generate a second image of the first type corresponding to a second respiratory state by applying the motion information to the first image of the first type.

The medical imaging apparatus may further include a display, and the controller may match at least one of the first and second images of the first type with at least one of the images of the second type. The display may display a matched image.

BRIEF DESCRIPTION OF THE DRAWINGS

Exemplary embodiments will now be described more fully hereinafter with reference to the accompanying drawings, in which reference numerals denote structural elements.

DETAILED DESCRIPTION

Figure 1:
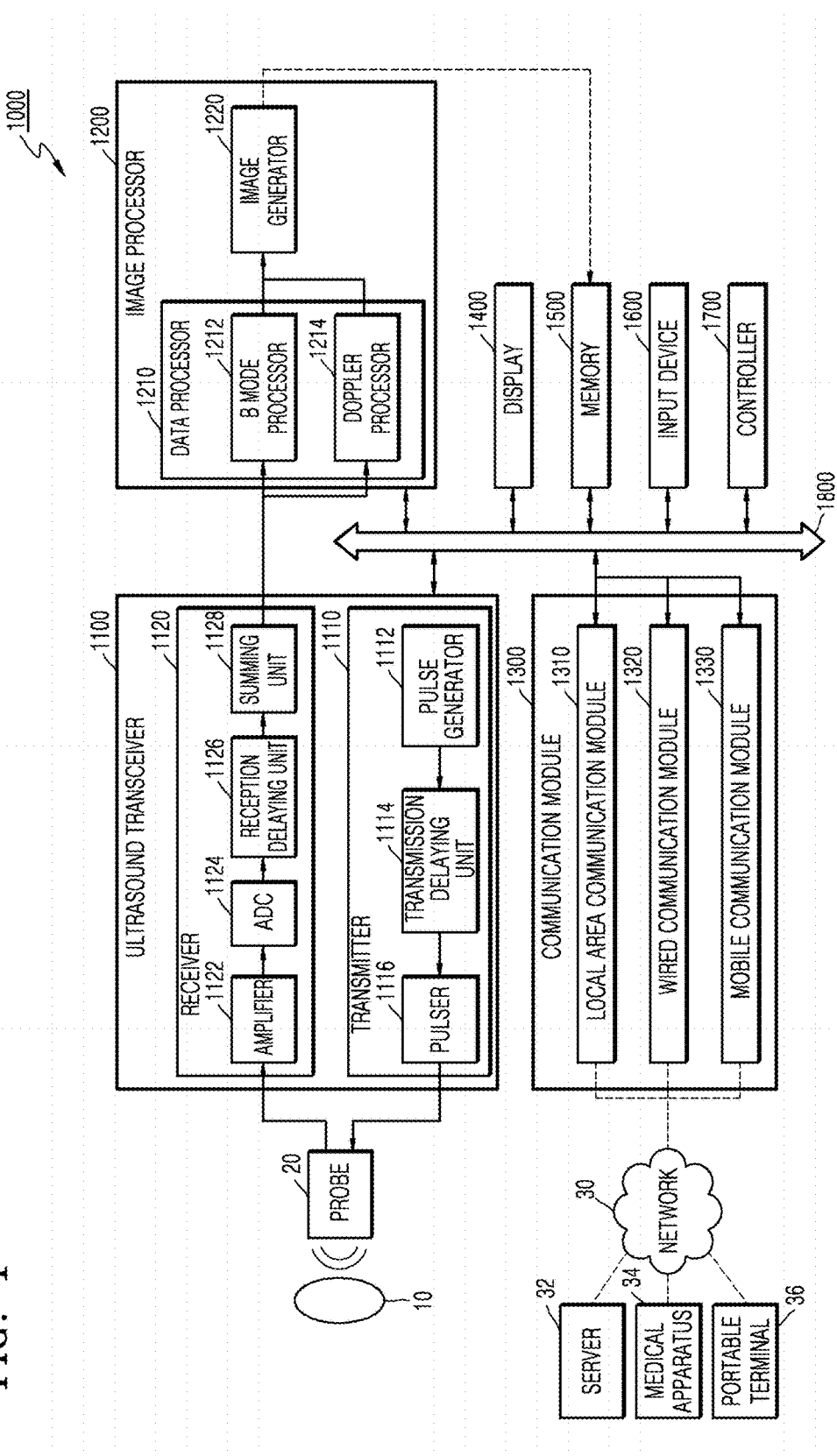
FIG. 1 is a block diagram of a configuration of an ultrasound diagnosis apparatus according to an exemplary embodiment.

All terms including descriptive or technical terms which are used herein should be construed as having meanings that are obvious to one of ordinary skill in the art. However, the terms may have different meanings according to the intention of one of ordinary skill in the art, precedent cases, or the appearance of new technologies. Also, some terms may be arbitrarily selected by the applicant, and in this case, the meaning of the selected terms will be described in detail in the detailed description of the invention. Thus, the terms used herein have to be defined based on the meaning of the terms together with the description throughout the specification.

Hereinafter, the terms used in the specification will be briefly described, and then the present invention will be described in detail.

The terms used in this specification are those general terms currently widely used in the art in consideration of functions regarding the present invention, but the terms may vary according to the intention of those of ordinary skill in the art, precedents, or new technology in the art. Also, specified terms may be selected by the applicant, and in this case, the detailed meaning thereof will be described in the detailed description of the invention. Thus, the terms used in the specification should be understood not as simple names but based on the meaning of the terms and the overall description of the invention.

When a part "includes" or "comprises" an element, unless there is a particular description contrary thereto, the part can further include other elements, not excluding the other elements. Also, the term "unit" in the embodiments of the inventive concept means a software component or hardware component such as a field-programmable gate array (FPGA) or an application-specific integrated circuit (ASIC), and performs a specific function. However, the term "unit" is not limited to software or hardware. The "unit" may be formed so as to be in an addressable storage medium, or may be formed so as to operate one or more processors. Thus, for example, the term "unit" may refer to components such as software components, object-oriented software components, class components, and task components, and may include processes, functions, attributes, procedures, subroutines, segments of program code, drivers, firmware, micro codes, circuits, data, a database, data structures, tables, arrays, or variables. A function provided by the components and "units" may be associated with the smaller number of components and "units", or may be divided into additional components and "units".

It will be understood that, although the terms "first", "second", etc. may be used herein to describe various elements, these elements should not be limited by these terms. These terms are only used to distinguish one element from another element. Thus, a first element discussed below could be termed a second element, and similarly, a second element could be termed a first element, without departing from the scope of example embodiments. As used herein, the term "and/or" includes any and all combinations of one or more of the associated listed items. Expressions such as "at least one of," when preceding a list of elements, modify the entire list of elements and do not modify the individual elements of the list.

Throughout the specification, an "image" may refer to multi-dimensional data composed of discrete image elements (e.g., pixels in a two-dimensional (2D) image and voxels in a three-dimensional (3D) image).

Throughout the specification, an "ultrasound image" refers to an image of an object, which is obtained using ultrasound waves. Ultrasound imaging apparatuses transmit ultrasound signals generated by transducers of a probe to an object and receive echo signals reflected from the object, thereby obtaining at least one image of an internal part of the object. Furthermore, an ultrasound image may take different forms. For example, the ultrasound image may be at least one of an amplitude (A) mode image, a brightness (B) mode image, a color (C) mode image, and a Doppler (D) mode image. In addition, the ultrasound image may be a 2D or 3D image.

Furthermore, an "object" may be a human, an animal, or a part of a human or animal. For example, the object may be an organ (e.g., the liver, heart, womb, brain, breast, or abdomen), a blood vessel, or a combination thereof. Also, the object may be a phantom. The phantom means a material having a density, an effective atomic number, and a volume that are approximately the same as those of an organism.

Throughout the specification, a "user" may be, but is not limited to, a medical expert, for example, a medical doctor, a nurse, a medical laboratory technologist, or a medical imaging expert, or a technician who repairs medical apparatuses.

Reference will now be made in detail to embodiments, examples of which are illustrated in the accompanying drawings. In this regard, the present embodiments may have different forms and should not be construed as being limited to the descriptions set forth herein.

FIG. 1 is a block diagram of a configuration of an ultrasound diagnosis apparatus 100 according to an exemplary embodiment.

Referring to FIG. 1, the ultrasound diagnosis apparatus 100 according to the present exemplary embodiment may include a probe 20, an ultrasound transceiver 115, an image processor 150, a display 160, a communication module 170, a memory 180, an input device 190, and a controller 195, which may be connected to one another via buses 185. The image processor 150 may include an image generator 155, a section information detector 130, and the display 160.

It will be understood by those of ordinary skill in the art that the ultrasound diagnosis apparatus 100 may further include common components other than those illustrated in FIG. 1.

In some embodiments, the ultrasound diagnosis apparatus 100 may be a cart type apparatus or a portable type apparatus. Examples of portable ultrasound diagnosis apparatuses may include, but are not limited to, a picture archiving and communication system (PACS) viewer, a smartphone, a laptop computer, a personal digital assistant (PDA), and a tablet PC.

The probe 20 transmits ultrasound waves to an object 10 in response to a driving signal applied by the ultrasound transceiver 115 and receives echo signals reflected by the object 10. The probe 20 includes a plurality of transducers, and the plurality of transducers oscillate in response to electric signals and generate acoustic energy, that is, ultrasound waves. Furthermore, the probe 20 may be connected to the main body of the ultrasound diagnosis apparatus 100 by wire or wirelessly, and according to embodiments, the ultrasound diagnosis apparatus 100 may include a plurality of probes 20.

A transmitter 110 supplies a driving signal to the probe 20. The transmitter 110 includes a pulse generator 112, a transmission delaying unit 114, and a pulser 116. The pulse generator 112 generates pulses for forming transmission ultrasound waves based on a predetermined pulse repetition frequency (PRF), and the transmission delaying unit 114 delays the pulses by delay times necessary for determining transmission directionality. The pulses which have been delayed correspond to a plurality of piezoelectric vibrators included in the probe 20, respectively. The pulser 116 applies a driving signal (or a driving pulse) to the probe 20 based on timing corresponding to each of the pulses which have been delayed.

A receiver 120 generates ultrasound data by processing echo signals received from the probe 20. The receiver 120 may include an amplifier 122, an analog-to-digital converter (ADC) 124, a reception delaying unit 126, and a summing unit 128. The amplifier 122 amplifies echo signals in each channel, and the ADC 124 performs analog-to-digital conversion with respect to the amplified echo signals. The reception delaying unit 126 delays digital echo signals output by the ADC 1124 by delay times necessary for determining reception directionality, and the summing unit 128 generates ultrasound data by summing the echo signals processed by the reception delaying unit 1126.

The image processor 150 generates an ultrasound image by scan-converting ultrasound data generated by the ultrasound transceiver 115.

The ultrasound image may be not only a grayscale ultrasound image obtained by scanning an object in an amplitude (A) mode, a brightness (B) mode, and a motion (M) mode, but also a Doppler image showing a movement of an object via a Doppler effect. The Doppler image may be a blood flow Doppler image showing flow of blood (also referred to as a color Doppler image), a tissue Doppler image showing a movement of tissue, or a spectral Doppler image showing a moving speed of an object as a waveform.

A B mode processor 141 extracts B mode components from ultrasound data and processes the B mode components. An image generator 155 may generate an ultrasound image indicating signal intensities as brightness based on the extracted B mode components 141.

Similarly, a Doppler processor 142 may extract Doppler components from ultrasound data, and the image generator 155 may generate a Doppler image indicating a movement of an object as colors or waveforms based on the extracted Doppler components.

According to an embodiment, the image generator 155 may generate a three-dimensional (3D) ultrasound image via volume-rendering with respect to volume data and may also generate an elasticity image by imaging deformation of the object 10 due to pressure. Furthermore, the image generator 155 may display various pieces of additional information in an ultrasound image by using text and graphics. In addition, the generated ultrasound image may be stored in the memory 180.

A display 160 displays the generated ultrasound image. The display 160 may display not only an ultrasound image, but also various pieces of information processed by the ultrasound diagnosis apparatus 100 on a screen image via a graphical user interface (GUI). In addition, the ultrasound diagnosis apparatus 100 may include two or more displays 160 according to embodiments.

The display 160 may include at least one of a liquid crystal display (LCD), a thin film transistor-LCD (TFT-LCD), an organic light-emitting diode (OLED) display, a flexible display, a 3D display, and an electrophoretic display.

Furthermore, when the display 160 and the input device 190 form a layer structure to form a touch screen, the display 160 may be used as an input device as well as an output device, via which a user inputs information via a touch.

The touch screen may be configured to detect a position of a touch input, a touched area, and pressure of a touch. The touch screen may also be configured to detect both a real touch and a proximity touch.

In the present specification, a 'real touch' means that a pointer actually touches a screen, and a 'proximity touch' means that a pointer does not actually touch a screen but approaches the screen while being separated from the screen by a predetermined distance. A 'pointer' used herein means a tool for touching a particular portion on or near a displayed screen. Examples of the pointer may include a stylus pen and a body part such as a finger.

Although not shown, the ultrasound diagnosis apparatus 100 may include various sensors that are disposed within or near the touch screen so as to sense a real touch or proximity touch on the touch screen. A tactile sensor is an example of the sensors for sensing a touch on the touch screen.

The tactile sensor is used to sense a touch of a particular object to the same or greater degree than the degree to which a human can sense the touch. The tactile sensor may detect various pieces of information including the roughness of a contact surface, the hardness of an object to be touched, the temperature of a point to be touched, etc.

A proximity sensor is another example of the sensors for sensing a touch. The proximity sensor refers to a sensor that senses the presence of an object that is approaching or is located near a predetermined detection surface by using the force of an electromagnetic field or infrared light without mechanical contact.

Examples of the proximity sensor include a transmissive photoelectric sensor, a direct reflective photoelectric sensor, a mirror reflective photoelectric sensor, a high-frequency oscillation proximity sensor, a capacitive proximity sensor, a magnetic proximity sensor, an infrared proximity sensor, and the like.

The communication module 170 is connected to a network 30 by wire or wirelessly to communicate with an external device or a server. The communication module 170 may exchange data with a hospital server or another medical apparatus in a hospital, which is connected thereto via a PACS. Furthermore, the communication module 170 may perform data communication according to the digital imaging and communications in medicine (DICOM) standard.

The communication module 170 may transmit or receive data related to diagnosis of an object, e.g., an ultrasound image, ultrasound data, and Doppler data of the object, via the network 30 and may also transmit or receive medical images captured by another medical apparatus, e.g., a computed tomography (CT) apparatus, a magnetic resonance imaging (MRI) apparatus, or an X-ray apparatus. Furthermore, the communication module 170 may receive information about a diagnosis history or medical treatment schedule of a patient from a server and utilizes the received information to diagnose the patient. Furthermore, the communication module 170 may perform data communication not only with a server or a medical apparatus in a hospital, but also with a portable terminal of a medical doctor or patient.

The communication module 170 is connected to the network 30 by wire or wirelessly to exchange data with a server 32, a medical apparatus 34, or a portable terminal 36. The communication module 170 may include one or more components for communication with external devices. For example, the communication module 1300 may include a local area communication module 171, a wired communication module 172, and a mobile communication module 173.

The local area communication module 171 refers to a module for local area communication within a predetermined distance. Examples of local area communication techniques according to an embodiment may include, but are not limited to, wireless LAN, Wi-Fi, Bluetooth, ZigBee, Wi-Fi Direct (WFD), ultra wideband (UWB), infrared data association (IrDA), Bluetooth low energy (BLE), and near field communication (NFC).

The wired communication module 172 refers to a module for communication using electric signals or optical signals. Examples of wired communication techniques according to an embodiment may include communication via a twisted pair cable, a coaxial cable, an optical fiber cable, and an Ethernet cable.

The mobile communication module 173 transmits or receives wireless signals to or from at least one selected from a base station, an external terminal, and a server on a mobile communication network. Here, the wireless signal may be a voice call signal, a video call signal, or data in any one of various formats according to transmission and reception of a text/multimedia message.

The memory 180 stores various data processed by the ultrasound diagnosis apparatus 100. For example, the memory 180 may store medical data related to diagnosis of an object, such as ultrasound data and an ultrasound image that are input or output, and may also store algorithms or programs which are to be executed in the ultrasound diagnosis apparatus 100.

The memory 180 may be any of various storage media, e.g., a flash memory, a hard disk drive, EEPROM, etc. Furthermore, the ultrasound diagnosis apparatus 100 may utilize web storage or a cloud server that performs the storage function of the memory 180 online.

The input device 190 generates input data that the user inputs for controlling an operation of the ultrasound diagnosis apparatus 100. The user input 190 may include hardware components, such as a keypad, a mouse, a touch pad, a track ball, and a jog switch. However, embodiments are not limited thereto, and the input device 1600 may further include any of various other input units including an electrocardiogram (ECG) measuring module, a respiration measuring module, a voice recognition sensor, a gesture recognition sensor, a fingerprint recognition sensor, an iris recognition sensor, a depth sensor, a distance sensor, etc.

In particular, the input device 190 may also include a touch screen in which a touch pad forms a layer structure with the display 160.

In this case, according to an exemplary embodiment, the ultrasound diagnosis apparatus 100 may display an ultrasound image in a predetermined mode and a control panel for the ultrasound image on a touch screen. The ultrasound diagnosis apparatus 100 may also sense a user's touch gesture performed on an ultrasound image via a touch screen.

According to an exemplary embodiment, the ultrasound diagnosis apparatus 100 may include some buttons that are frequently used by a user among buttons that are included in a control panel of a general ultrasound apparatus, and provide the remaining buttons in the form of a graphical user interface (GUI) via a touch screen.

The controller 195 may control all operations of the ultrasound diagnosis apparatus 100. In other words, the controller 195 may control operations among the probe 20, the ultrasound transceiver 100, the image processor 150, the communication module 170, the memory 180, and the input device 190 shown in FIG. 1.

All or some of the probe 20, the ultrasound transceiver 115, the image processor 150, the communication module 170, the memory 180, the user input 190, and the controller 195 may be implemented as software modules. However, embodiments of the present invention are not limited thereto, and some of the components stated above may be implemented as hardware modules. Also, at least one of the ultrasound transmission/reception unit 115, the image processor 150, and the communication module 170 may be included in the control unit 195; however, the inventive concept is not limited thereto.

Figure 2:
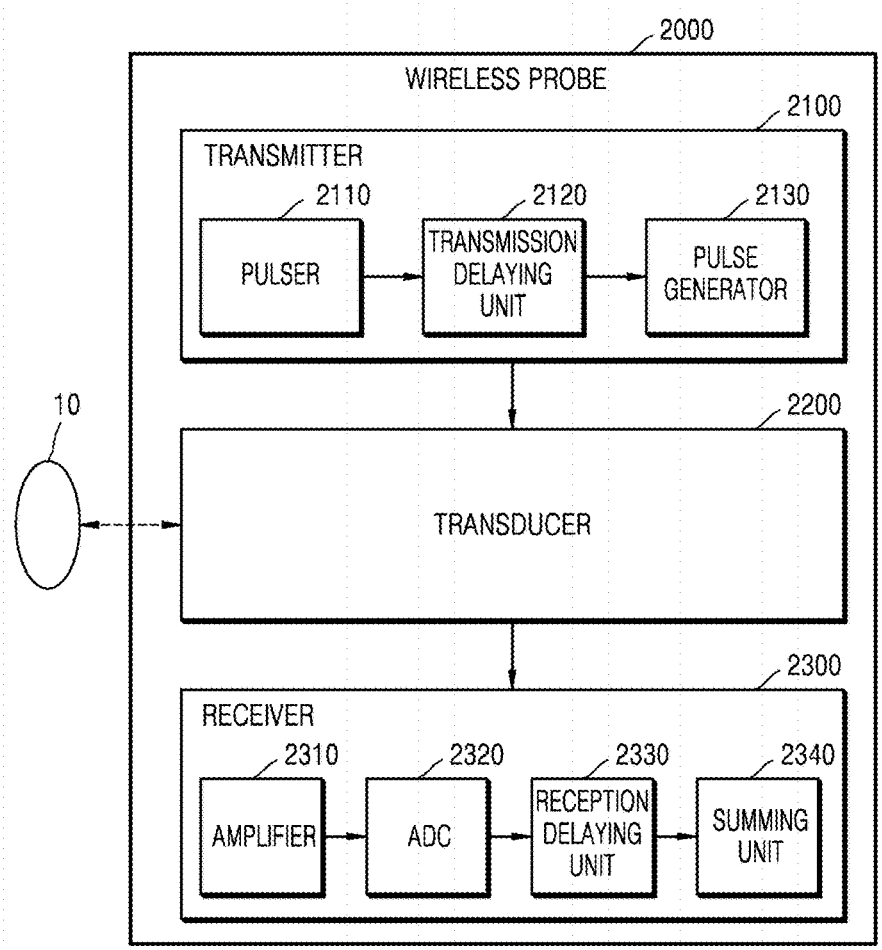
FIG. 2 is a block diagram of a configuration of a wireless probe according to an exemplary embodiment.

FIG. 2 is a block diagram showing a configuration of a wireless probe 2000 according to an embodiment. As described above with reference to FIG. 1, the wireless probe 2000 may include a plurality of transducers, and, according to embodiments, may include some or all of the components of the ultrasound transceiver 100 shown in FIG. 1.

The wireless probe 2000 according to the embodiment shown in FIG. 2 includes a transmitter 2100, a transducer 2200, and a receiver 2300. Since descriptions thereof are given above with reference to FIG. 1, detailed descriptions thereof will be omitted here. In addition, according to embodiments, the wireless probe 2000 may selectively include a reception delaying unit 2330 and a summing unit 2340.

The wireless probe 2000 may transmit ultrasound signals to the object 10, receive echo signals from the object 10, generate ultrasound data, and wirelessly transmit the ultrasound data to the ultrasound diagnosis apparatus 1000 shown in FIG. 1.

The wireless probe 2000 may be a smart device including a transducer array that is capable of performing an ultrasound scan. In detail, the wireless probe 2000 is a smart device that acquires ultrasound data by scanning an object via the transducer array. Then, the wireless probe 2000 may generate an ultrasound image by using the acquired ultrasound data and/or display the ultrasound image. The wireless probe 2000 may include a display via which a screen including at least one ultrasound image and/or a user interface screen for controlling an operation of scanning an object may be displayed.

While the user is scanning a predetermined body part of a patient that is an object by using the wireless probe 2000, the wireless probe 2000 and the ultrasound diagnosis apparatus 100 may continue to transmit or receive certain data therebetween via a wireless network. In detail, while the user is scanning a predetermined body part of a patient that is an object by using the wireless probe 2000, the wireless probe 2000 may transmit ultrasound data to the ultrasound diagnosis apparatus 100 in real-time via the wireless network. The ultrasound data may be updated in real-time as an ultrasound scan continues and then be transmitted from the wireless probe 2000 to the ultrasound diagnosis apparatus 100.

Figure 3:
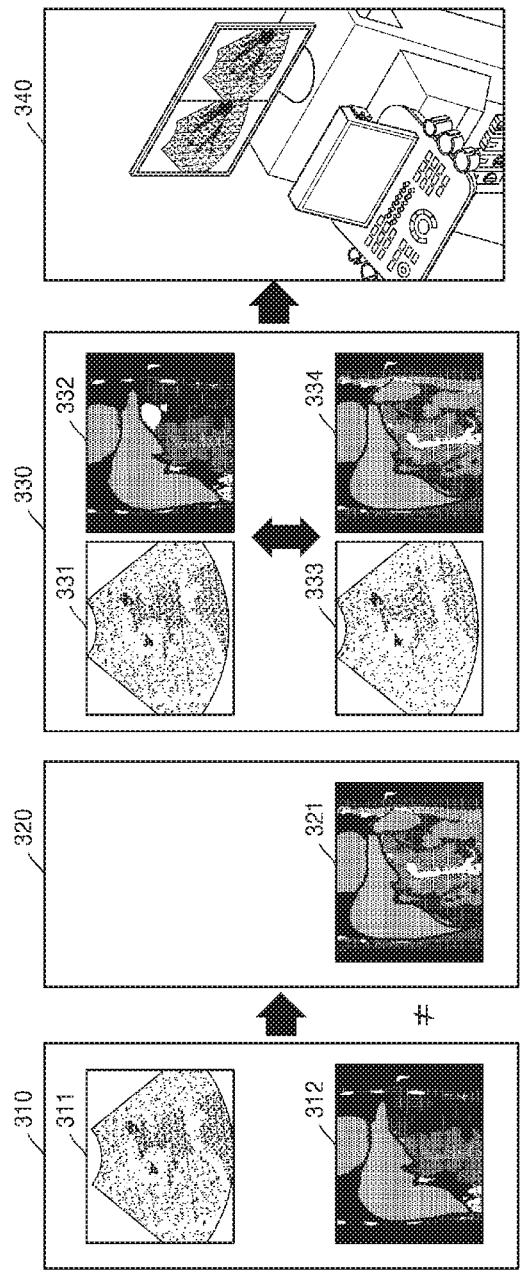
FIG. 3 is a conceptual diagram for explaining an operation of a medical imaging apparatus for matching a computed tomography (CT) image with an ultrasound image, according to an exemplary embodiment.

FIG. 3 is a conceptual diagram for explaining an operation of a medical imaging apparatus for matching a computed tomography (CT) image with an ultrasound image, according to an exemplary embodiment.

The medical imaging apparatus may match images of first and second types with each other. In this case, the images are of different types, that is, the first type is different from the second type. For example, the image of the first type may be one of an ultrasound image, an optical coherence tomography (OCT) image, a CT image, a magnetic resonance (MR)

image, an X-ray image, a single photon emission computed tomography (SPECT) image, a positron emission tomography (PET) image, a C-arm image, a PET-CT image, a PET-MR image, and a fluoroscopy image. It will be understood by those of ordinary skill in the art that the image of the first type is not limited thereto, and may further include other types of images.

In the present specification, even when the images of the first and second types are referred to as a CT image and an ultrasound image, respectively, the medical imaging apparatus may match not only the CT and ultrasound images but also the other above-described types of images with each other.

FIG. 3 is a schematic diagram for explaining a flow of operations performed by a medical imaging apparatus for matching CT and ultrasound images.

Referring to 310 of FIG. 3, the medical imaging apparatus may acquire a first image of a first type and a first image of a second type. For example, the medical imaging apparatus may acquire an ultrasound image 311 and a CT image 312 that are captured images of the same object. The medical imaging apparatus may acquire the ultrasound image 311 and the CT image 312 by directly photographing an object or receive them from an external device.

In general, a CT image and an ultrasound image are captured when an object is in a (deep) inspiratory state and an expiratory state, respectively. In this case, anatomical features of the object and/or a position of a structure in the object may change according to a respiratory state of the object. Thus, anatomical features of the object in a first image of a first type may be different from those in a second image of a second type, or a position of a structure in the first image may not coincide with that in the second image. In this case, if the medical imaging apparatus matches the first image of the first type with the second image of the second type, an error may occur with respect to the anatomical features of the object or the position of the structure in the first and second images. Thus, whether the anatomical features of the object and/or a position of a structure in different types of images coincide with each other may be a criterion for matching the different types of images. Furthermore, a respiratory state of the object in which different types of images are captured may be a criterion for matching the images.

Referring to 320 of FIG. 3, the medical imaging apparatus may generate an image 321) of a first type to be matched with the first image of the second type. For example, in detail, since anatomical features of the object and/or a position of a structure may vary according to whether the object is in an inspiratory or expiratory state, the medical imaging apparatus may match images captured when the object is in the same respiratory state. The medical imaging apparatus may generate an image of the first type corresponding to the same respiratory state as that depicted in the first image of the second type.

To generate a second image of the first type to be matched with a second image of the second type, the medical imaging apparatus may determine motion information between the first and second images of the second type and apply the motion information to the first image of the first type.

Referring to 330 of FIG. 3, the medical imaging apparatus may match different types of images. The medical imaging apparatus may match a set of the first images of the first and second types and a set of the second images of the first and second types, respectively. In this case, each set of images being matched may be captured in the same respiratory state.

For example, the medical imaging apparatus may match a set of an ultrasound image 331 and a CT image 332 corresponding to an expiratory state and a set of an ultrasound image 333 and a CT image 334 corresponding to an inspiratory state, respectively.

Referring to 340 of FIG. 3, the medical imaging apparatus may display a matched image. Furthermore, the medical imaging apparatus may display a plurality of images before they are each matched, together with the matched image.

Figure 4A:
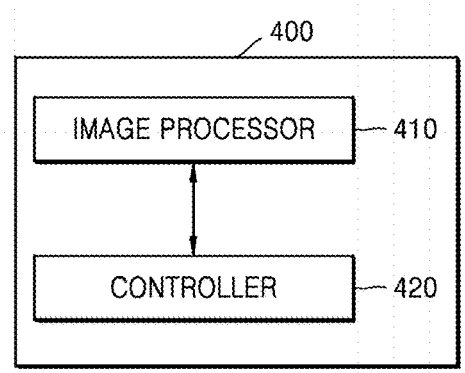
FIG. 4A is a block diagram of a configuration of a medical imaging apparatus according to an exemplary embodiment.

FIG. 4A is a block diagram of a configuration of a medical imaging apparatus 400 according to an exemplary embodiment.

The medical imaging apparatus according to the present exemplary embodiment may include an image processor 410 and a controller 420. However, all the components shown in FIG. 4A are not essential components. The medical imaging apparatus 400 may include more or fewer components than those shown in FIG. 4A.

The image processor 410 may acquire a first image of a first type captured in a first respiratory state of an object. In detail, the image processor 410 may acquire an image of the object by photographing or scanning the object or receive an image of the object from an external device.

In this case, the external device may be physically independent of the medical imaging apparatus 400. The external device is a device for acquiring, storing, processing, or using data related to an image of an object, and may be a medical server, a portable terminal, or any other computing device for using and processing a medical image. For example, the external device may be a medical diagnosis apparatus included in a medical institution such as a hospital. Furthermore, the external device may be a server in a hospital for recording and storing a patient's clinical history, the medical imaging apparatus 400 used by a medical doctor in a hospital to read a medical image, or the like.

Furthermore, the image processor 410 may acquire a first image of a second type captured in the first respiratory state of the object and a second image of the second type captured in a second respiratory state thereof. Like in the case of images of the first type, to obtain images of the second type, the image processor 410 may acquire an image of the object by photographing or scanning the object, or receive an image of the object from the external device. In this case, the images of the second type are different from those of the first type.

Furthermore, the image processor 410 may acquire images of the second type captured in a plurality of respiratory states of the object. The plurality of respiratory states may include first through third respiratory states, and are not limited thereto. A respiratory state may be classified into a plurality of respiratory states depending on the degree of breathing of the object.

According to an exemplary embodiment, images of the first and second types are a CT image and an ultrasound image, respectively. In addition, one of ordinary skill in the art will understand that the images of the first and second types may be any different types of images and are not limited to the CT image and the ultrasound image, respectively.

Furthermore, the first and second respiratory states may be inspiratory and expiratory states of the object, respectively. In this case, a respiratory state is merely classified into the first and second respiratory states according to the degree of breathing, but this is merely an example. The respiratory state may be classified into a plurality of respiratory states according to another criterion.

The controller 420 may determine motion information of the object with respect to a respiratory state, based on the first and second images of the second type respectively corresponding to the first and second respiratory states of the object.

In detail, the controller 420 may determine at least one parameter for obtaining motion information indicating a spatial transformation between the first and second images of the second type. The controller 420 may determine at least one parameter that minimizes a spatial transformation between the first and second images of the second type. In this case, the spatial transformation may be based on at least one of a position, rotation, and a size of the object. The controller 420 may determine motion information based on the determined at least one parameter.

To determine the spatial transformation between the first and second images of the second type, the controller 420 may calculate a difference between the first and second images. The difference between the first and second images of the second type may be calculated using Equation (1):

$$\text{Sum}((I(p)-I'(T^*p))^2)/N \tag{1}$$

where T, P, and N respectively denote a spatial transformation, a spatial position, and the number of pixels. The difference between the first and second images may be calculated using a difference between pixel values as well as various image properties that may be extracted from an image, such as an image texture, a histogram, etc.

For example, the controller 420 may determine a value of a parameter that minimizes a spatial transformation between the first and second images of the second type. In this case, one of ordinary skill in the art will understand not only that a value of a parameter may be determined if a spatial transformation is minimized but also that if the spatial transformation satisfies a predetermined condition, a value of a parameter may be determined according to the predetermined condition.

The controller 420 may also update a parameter describing a spatial transformation so as to reduce a difference between the first and second images. In this case, the controller 420 may repeat a process of calculating the difference between the first and second images and updating the parameter.

Furthermore, properties of an anatomical structure extracted from each of the first and second images of the second type may be used in determining the spatial transformation between the first and second images of the second type. The controller 420 may determine the spatial transformation therebetween by using properties of an anatomical structure extracted from each of the first and second images. In detail, at least one of a pixel value difference, an image texture, and a histogram may be used in extracting properties of an anatomical structure and/or determining the spatial transformation between the first and second images, and exemplary embodiments are not limited thereto. In other words, various factors that may be extracted from each of the first and second images may be used in determining the spatial transformation therebetween.

Furthermore, the controller 420 may acquire position information of the object and determine motion information based on the first and second images of the second type respectively corresponding to first and second respiratory states corresponding to the acquired position information. In this case, the position information may be acquired from a sensor. The sensor may be built into or physically separate from the medical imaging apparatus 400. The position information may be acquired from the sensor as well as another external device.

The controller 420 may determine motion information of the object with respect to a respiratory state, based on position information of the object and images of the second type respectively corresponding to a plurality of respiratory states. The controller 420 may generate a second image of a first type corresponding to the second respiratory state by applying the motion information to the first image of the first type. Furthermore, the controller 420 may determine motion information by using anatomical structures included in images of the second type.

For example, the controller 420 may determine the degree of transformation for a respiratory state by using position information of the object and ultrasound images thereof. The position information of the object may be acquired from a sensor and may be detected by acquiring position information and ultrasound images with respect to time while free breathing is being performed for a specific time. In this case, examples of the sensor may include an electronic sensor, an optical sensor, etc. for measuring a position and respiration of the object, and types of the sensor are not limited thereto. Furthermore, the sensor may be attached to an ultrasound probe and measure a position and respiration of the object. In detail, the controller 420 may acquire times when specific directions detected by the sensor (text: specific directions of the sensor?) correspond to inspiratory and expiratory states, respectively, and determine motion vectors from ultrasound images corresponding to the acquired times.

The controller 420 may determine the degree of transformation in a respiratory state by using ultrasound images. The controller 420 may acquire ultrasound images with respect to time while free breathing is being performed for a specific time and extract anatomical structures or image properties from the acquired ultrasound images, thereby determining a spatial transformation between the ultrasound images. The controller 420 may determine motion information (e.g., motion vectors) based on the degree of transformation determined for the respiratory state.

The controller 420 may generate a second image of the first type corresponding to the second respiratory state by applying the motion information to the first image of the first type.

In addition, the controller 420 may match at least one of the first and second images of the first type with at least one of the first and second images of the second type. The controller 420 may select images of the first and second types according to a predetermined algorithm or criterion for registration. Furthermore, as described below with reference to FIG. 4B, the controller 420 may match images of the first and second types with each other based on a user input.

When images corresponding to the same respiratory state overlap each other, positions of the object in the images may accurately coincide with each other, compared to when images corresponding to different respiratory states overlap. Thus, the controller 420 may match images of the first and second types corresponding to the same respiratory state together.

The medical imaging apparatus 400 may include a central arithmetic processor that controls overall operations of the image processor 410 and the controller 420. The central arithmetic processor may be implemented as an array of a plurality of logic gates or a combination of a general purpose microprocessor and a program that can be run on the general purpose microprocessor. Furthermore, it will be appreciated by those of ordinary skill in the art to which the present embodiment pertains that the central arithmetic processor may be formed by different types of hardware.

Figure 4B:
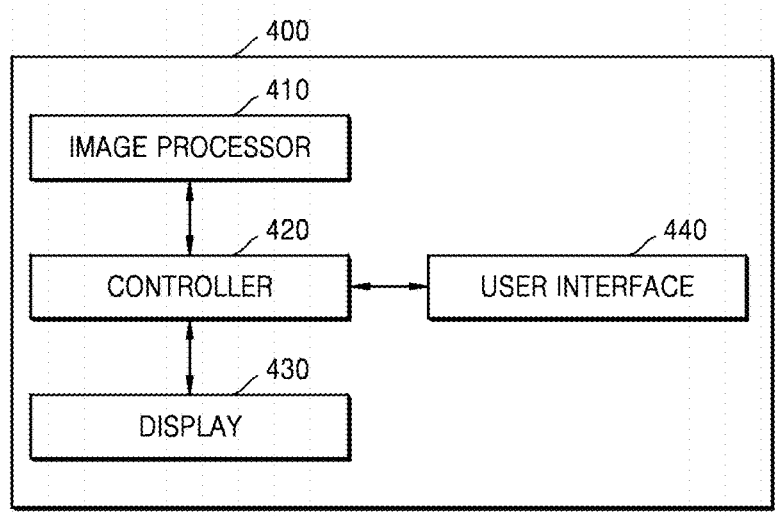
FIG. 4B is a block diagram of a configuration of a medical imaging apparatus according to another exemplary embodiment.

FIG. 4B is a block diagram of a configuration of a medical imaging apparatus 400 according to another exemplary embodiment.

Referring to FIG. 4B, unlike the medical imaging apparatus 400 of FIG. 4A, the medical imaging apparatus 400 according to the present exemplary embodiment may further include a display 430 and a user interface 440.

Since an image processor 410 and a controller 420 of the medical imaging apparatus 400 of FIG. 4B respectively correspond to the image processor 410 and the controller 420 of the medical imaging apparatus 400 of FIG. 4A, the same descriptions as already provided with respect to FIG. 4A will be omitted below.

The display 430 may display at least one of first and second images of a first type and at least one of first and second images of a second type.

The display 430 may display at least two of the first and second images of the first type and the first and second images of the second type in such a manner that they overlap each other. For example, the display 430 may display the first images of the first and second types in such a manner that they overlap each other.

The controller 420 controls the display 430 to display a predetermined screen. The display 430 may display the predetermined screen so that a user or patient may visually recognize a predetermined image or information. The display 430 may correspond to the display 160 shown in FIG. 1 or be separate from the ultrasound diagnosis apparatus 100 of FIG. 1.

The display 430 may display a predetermined screen. In detail, the display 430 may display the predetermined screen according to control by the controller 420. The display 430 includes a display panel (not shown) and displays a user interface screen, a medical image screen, etc. on the display panel.

The user interface 440 may receive a user input for selecting different types of images to be matched. In detail, the user interface 440 may receive a first user input for selecting at least one from among first and second images of a first type and a second user input for selecting at least one from among first and second images of a second type.

The user interface 440 refers to a device via which data for controlling the medical imaging apparatus 400 is received from a user. The user interface 440 may include hardware components, such as a keypad, a mouse, a touch panel, a touch screen, a track ball, and a jog switch, but is not limited thereto. The user interface 440 may further include any of various other input units including an electrocardiogram (ECG) measuring module, a respiration measuring module, a voice recognition sensor, a gesture recognition sensor, a fingerprint recognition sensor, an iris recognition sensor, a depth sensor, a distance sensor, etc.

The user interface 440 may generate and output a user interface screen for receiving a predetermined command or data from the user. The user interface 440 may also receive the predetermined command or data from the user via the user interface screen. The user may view the user interface screen displayed via the display 430 to visually recognize predetermined information and input a predetermined command or data via the user interface 440.

For example, the user interface 440 may be formed as a touch pad. In detail, the user interface 440 includes a touch pad (not shown) combined with the display panel in the display 430. In this case, a user interface screen is output to the display panel. When a predetermined command is input via the user interface screen, the touch pad may detect information about the predetermined command and then transmit the detected information to the controller 420. Then, the controller 420 may interpret the detected information to recognize and execute the predetermined command input by the user.

The medical imaging apparatus 400 may further include a storage unit (not shown) and a communication module (not shown). The storage unit may store data related to an object (e.g., an ultrasound image, ultrasound data, scan-related data, data related to diagnosis of a patient, etc.), data transmitted from an external device to the medical imaging apparatus 400, etc. The data transmitted from the external device may include patient-related information, data necessary for diagnosis and treatment of a patient, a patient's past medical history, a medical work list corresponding to instructions regarding diagnosis of a patient, and the like.

The communication module may receive and/or transmit data from and/or to an external device. For example, the communication module may connect to a wireless probe or an external device via a communication network based on Wi-Fi or Wi-Fi Direct (WFD) technology. In detail, examples of a wireless communication network to which the communication module can connect may include, but are not limited to, Wireless LAN (WLAN), Wi-Fi, Bluetooth, ZigBee, WFD, Ultra Wideband (UWB), Infrared Data Association (IrDA), Bluetooth Low Energy (BLE), and Near Field Communication (NFC).

In this case, the ultrasound imaging apparatus 400 may obtain a plurality of types of images respectively corresponding to respiratory states by directly photographing or scanning an object or receiving them from an external device. The external device may be a storage device. The storage device may be any of various storage media such as a hard disk drive (HDD), Read Only Memory (ROM), Random Access Memory (RAM), a flash memory, and a memory card.

Hereinafter, various operations performed by the medical imaging apparatus 400 and applications thereof will be described in detail. Although none of the image processor 410, the controller 420, and the display 430 are specified, features and aspects that would be clearly understood by and are obvious to those of ordinary skill in the art may be considered as a typical implementation. The scope of the present inventive concept is not limited by a name of a particular component or physical/logical structure.

Figure 5A:
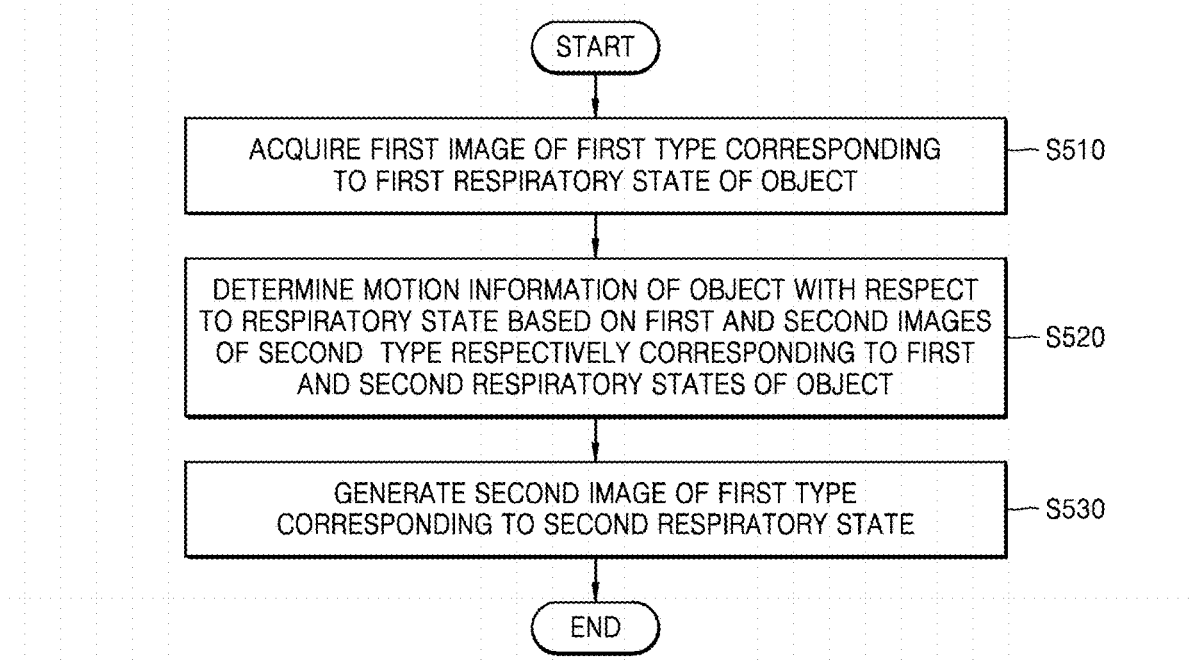
FIG. 5A is a flowchart of a method of operating a medical imaging apparatus, according to an exemplary embodiment.

FIG. 5A is a flowchart of a method of operating the medical imaging apparatus 400, according to an exemplary embodiment.

Referring to FIG. 5A, the medical imaging apparatus 400 may acquire a first image of a first type corresponding to a first respiratory state (S510). For example, the medical imaging apparatus 400 may acquire a first CT image captured when an object is in an inspiratory state. In general, a CT image is captured in a state in which air has been inhaled for examination of a lesion. Thus, the medical imaging apparatus 400 may generate a CT image corresponding to an inspiratory state by using motion vectors of different types of images than the CT image. When the medical imaging apparatus 400 is a CT apparatus, the medical imaging apparatus 400 may acquire a CT image by directly photographing an object. Furthermore, the medical imaging apparatus 400 may acquire a CT image from an external device.

The medical imaging apparatus 400 may determine motion information of the object with respect to a respiratory state, based on first and second images of a second type respectively corresponding to the first respiratory state and a second respiratory state of the object (S520).

For example, the medical imaging apparatus 400 may acquire first and second ultrasound images respectively corresponding to inspiratory and expiratory states. The medical imaging apparatus 400 may determine at least one parameter for obtaining motion information indicating a spatial transformation between the first and second ultrasound images, and determine a value of the at least one parameter based on the spatial transformation. The medical imaging apparatus 400 may determine motion information (e.g., a motion vector) based on the determined value of the at least one parameter).

As another example, the medical imaging apparatus 400 may acquire position information of the object and determine motion information based on the first and second ultrasound images respectively acquired in the inspiratory and expiratory states corresponding to the acquired position information.

Furthermore, the medical imaging apparatus 400 may acquire position information of the object and determine motion information of the object with respect to a respiratory state based on the position information and images of the second type respectively corresponding to a plurality of respiratory states. The motion information may be determined based on the position information of the object and anatomical structures in the images of the second type.

The medical imaging apparatus 400 may generate a second image of the first type corresponding to the second respiratory state (S530). In detail, the medical imaging apparatus 400 may generate the second image of the first type corresponding to the secondary respiratory state by applying the motion information to the first image of the first type.

For example, the medical imaging apparatus 400 may acquire motion information indicating a structural or spatial transformation of the object from first and second ultrasound images respectively corresponding to inspiratory and expiratory states. The medical imaging apparatus 400 may generate a second CT image corresponding to the expiratory state by applying the motion information to a first CT image captured in the inspiratory state.

In addition, a non-transitory computer-readable recording medium having recorded thereon a program for performing a method of operating the medical imaging apparatus 400 may include codes representing the method. In detail, the codes may include a code for acquiring a first image of a first type corresponding to a first respiratory state of an object, a code for determining motion information of the object with respect to a respiratory state based on first and second images of a second type, and a code for generating a second image of the first type corresponding to a secondary respiratory state by applying the motion information to the first image of the first type, but the codes are not limited thereto.

Figure 5B:
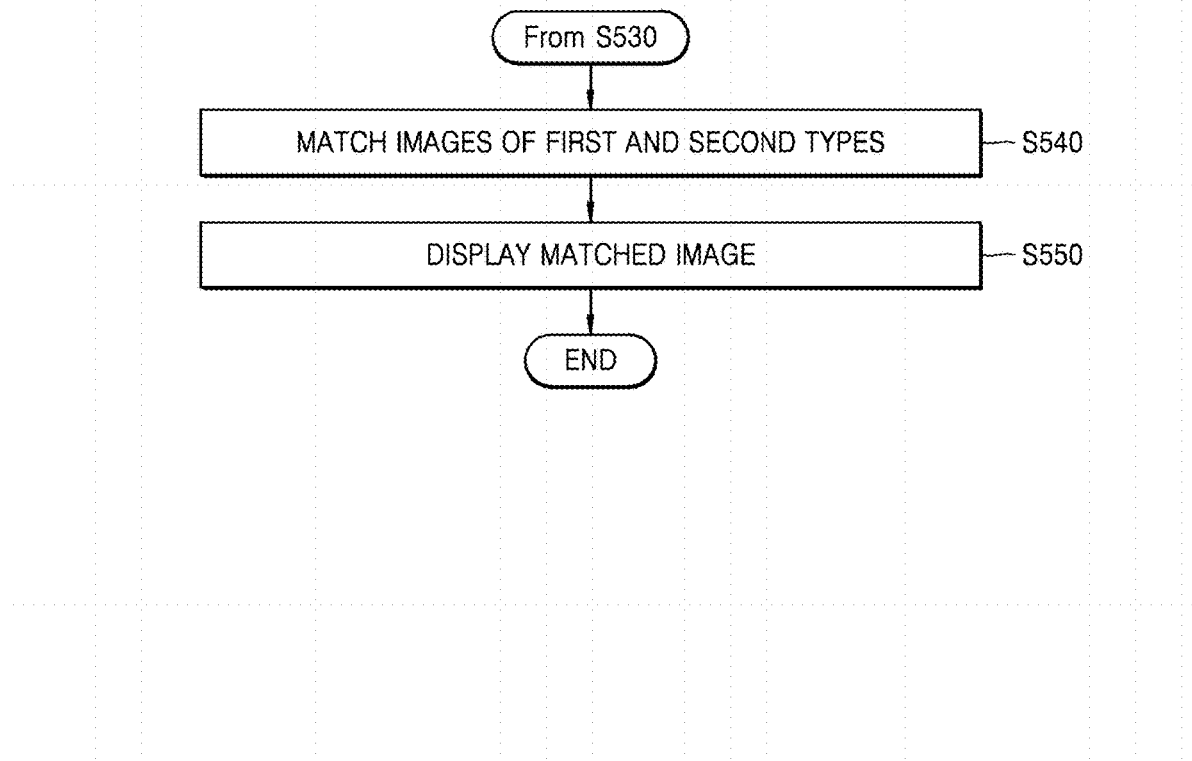
FIG. 5B is a flowchart of a method of operating a medical imaging apparatus, according to another exemplary embodiment.

FIG. 5B is a flowchart of a method of operating the medical imaging apparatus 400, according to another exemplary embodiment.

Referring to FIG. 5B, the medical imaging apparatus 400 may match images of first and second types together (S540). The medical imaging apparatus 400 may match at least one of first and second images of the first type and at least one of first and second images of the second type. In detail, the medical imaging apparatus 400 may match the second image of the first type with the first image of the second type.

For example, the medical imaging apparatus 400 may match a second CT image corresponding to an expiratory state with a second ultrasound image corresponding to the expiratory state. Furthermore, the medical imaging apparatus 400 may match a first CT image corresponding to an inspiratory state with a first ultrasound image corresponding to the inspiratory state. In addition, the medical imaging apparatus 400 may match different types of images respectively corresponding to different respiratory states.

Furthermore, the medical imaging apparatus 400 may match at least one of first and second images of the first type with at least one of images of the second type.

The medical imaging apparatus 400 may display a matched image (S550). Furthermore, the medical imaging apparatus 400 may display the matched image together with images before they are matched.

In addition, a non-transitory computer-readable recording medium having recorded thereon a program for performing a method of operating the medical imaging apparatus 400 may include codes representing the method. In detail, the codes may include a code for matching images of first and second types together and a code for displaying a matched image, but the codes are not limited thereto.

Figure 5C:
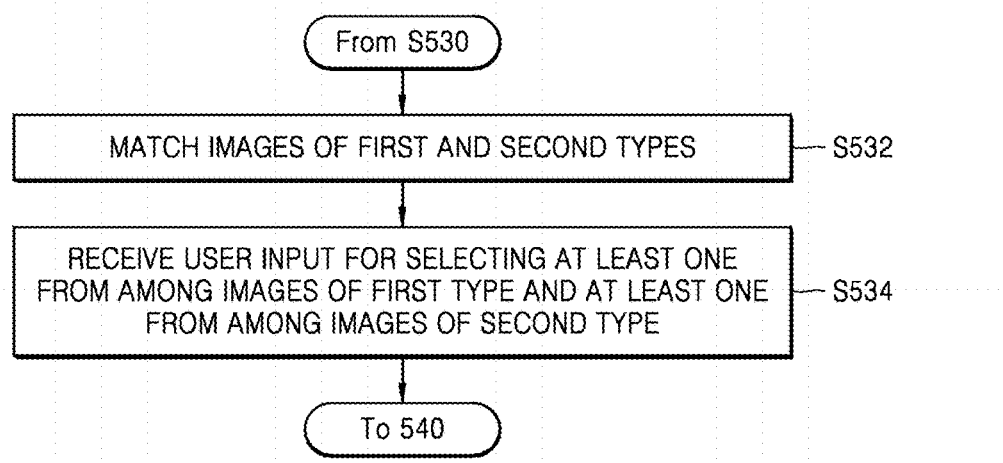
FIG. 5C is a flowchart of a method of operating a medical imaging apparatus, according to another exemplary embodiment.

FIG. 5C is a flowchart of a method of operating the medical imaging apparatus 400, according to another exemplary embodiment. FIG. 5C is a flowchart for explaining a process of receiving a user input for selecting images to be matched from among different types of images.

Referring to FIG. 5C, the medical imaging apparatus 400 may display images of a first type and images of a second type (S532). The medical imaging apparatus 400 may display some of a plurality of images of the first type and/or some of a plurality of images of the second type.

The medical imaging apparatus 400 may display at least one of a plurality of images of the first type and at least one of a plurality of images of the second type in such a manner that they overlap each other.

Furthermore, the medical imaging apparatus 400 may display at least two of a plurality of images of the first type in the overlapping manner while displaying at least two of a plurality of images of the second type in the overlapping manner.

The medical imaging apparatus 400 may receive a user input for selecting at least one image from among the images of the first type and at least one image from among the images of the second type (S534).

The medical imaging apparatus 400 may receive a user input for selecting a second ultrasound image and a second CT image, both of which correspond to an expiratory state. The medical imaging apparatus 400 may match the second ultrasound image corresponding to the expiratory state with the second CT image corresponding to the expiratory state, based on the user input.

In addition, a non-transitory computer-readable recording medium having recorded thereon a program for performing a method of operating the medical imaging apparatus 400 may include codes representing the method. In detail, the codes may include a code for matching images of first and second types together and a code for receiving a user input for selecting at least one image from among images of the first type and at least one image from among images of the second type, but the codes are not limited thereto.

FIGS. 6A through 6D are diagrams for explaining a first image of a first type, corresponding to a first respiratory state of an object, and a second image of the first type, corresponding to a second respiratory state and being acquired from the first image of the first type, according to an exemplary embodiment.

The medical imaging apparatus 400 may provide a cross-sectional image of an object and display an internal structure (e.g., the heart, liver, stomach, etc.) without superimposition of adjacent structures.

Figure 6A:
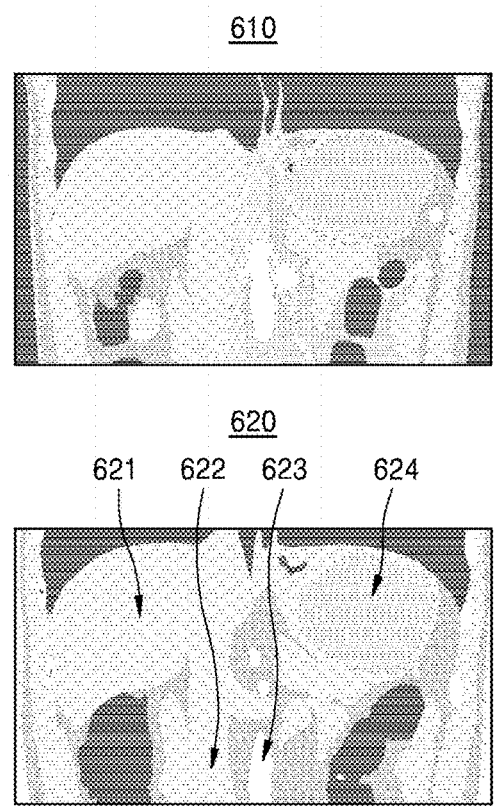
FIGS. 6A through 6D are diagrams for explaining a first image of a first type, corresponding to a first respiratory state of an object, and a second image of the first type, corresponding to a second respiratory state and being acquired from the first image of the first type, according to an exemplary embodiment.

Referring to FIG. 6A, the medical imaging apparatus 400 may acquire a first CT image 610 captured in an inspiratory state and showing a liver 621 and a stomach 624 of a human. A CT image may be generally captured in an inspiratory state. The medical imaging apparatus 400 may generate a second CT image 620 corresponding to an expiratory state by using different types of images than a CT image. In this case, the different types of images may be first and second ultrasound images respectively corresponding to inspiratory and expiratory states. It will be obvious to those of ordinary skill in the art that the different types of images are not limited to ultrasound images. As shown in FIG. 6A, structural or spatial positions of the liver 621, an inferior vena cava 622, an aorta 623, the stomach 624, etc. may vary according to a respiratory state.

Figure 6B:
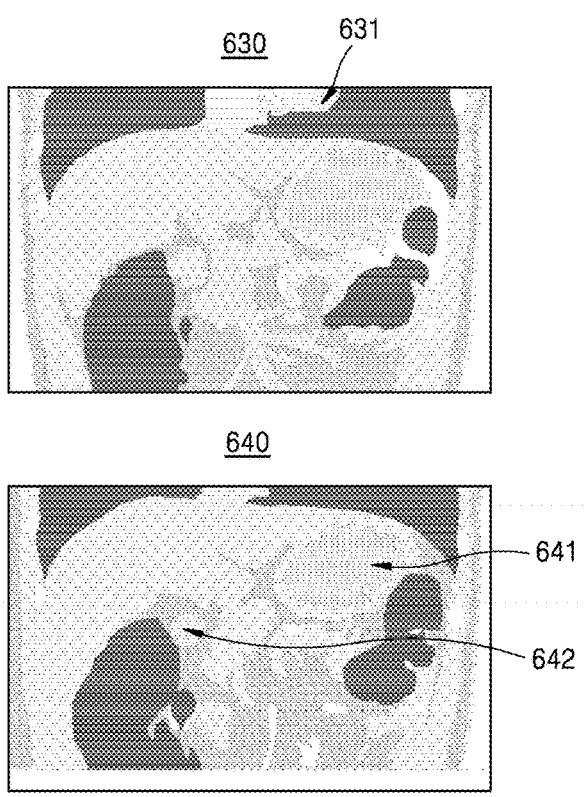

Referring to FIG. 6B, the medical imaging apparatus 400 may acquire a first CT image 630 captured in an inspiratory state and showing a heart 631, a stomach 641, and a kidney 642 of the human. The medical imaging apparatus 400 may generate a second CT image 640 corresponding to the inspiratory state by using different types of images than a CT image. As shown in FIG. 6B, structural or spatial positions of the heart 631, the stomach 641, and the kidney 642 may vary according to a respiratory state.

Figure 6C:
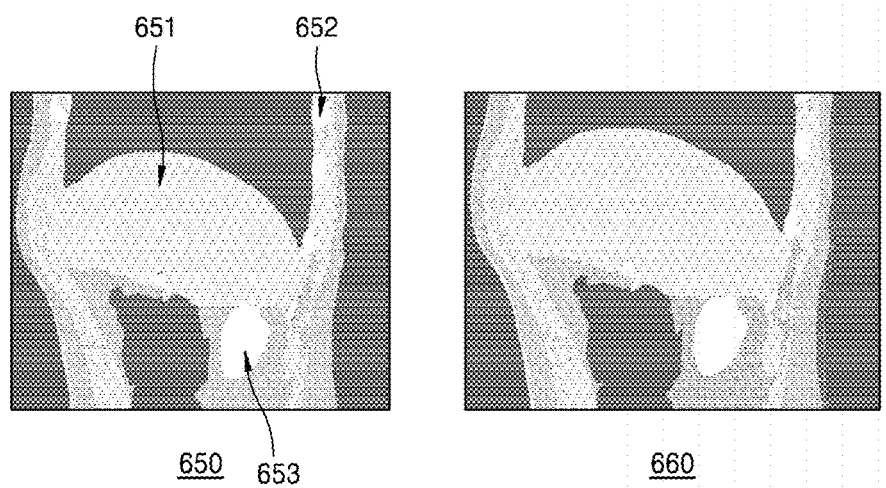

Referring to FIG. 6C, the medical imaging apparatus 400 may acquire a first CT image 650 captured in an inspiratory state and showing a liver 651, a spine 652, and a kidney 653 of the human. The medical imaging apparatus 400 may generate a second CT image 660 corresponding to an expiratory state by using different types of images than a CT image. As shown in FIG. 6C, structural or spatial positions of the liver 651, the spine 652, and the kidney 653 may vary according to a respiratory state.

Figure 6D:
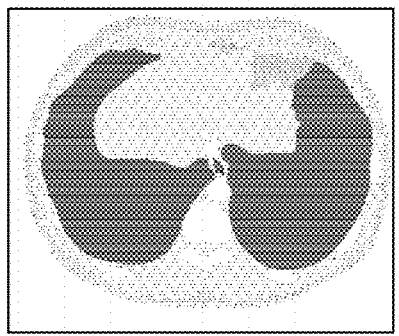
Figure 6D:
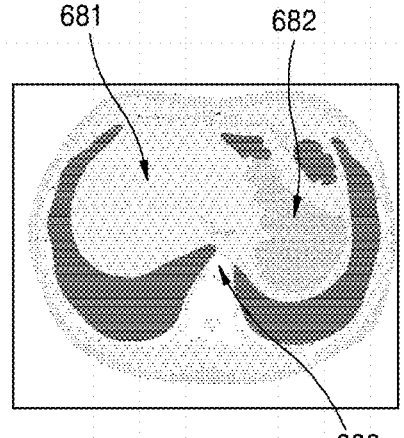

Referring to FIG. 6D, the medical imaging apparatus 400 may acquire a first CT image 670 captured in an inspiratory state and showing a liver 681, a stomach 682, and an aorta 683 of the human. The medical imaging apparatus 400 may generate a second CT image 680 corresponding to an expiratory state by using different types of images than a CT image. As shown in FIG. 6D, structural or spatial positions of the liver 681, the stomach 682, and the aorta 683 may vary according to a respiratory state.

Figure 7:
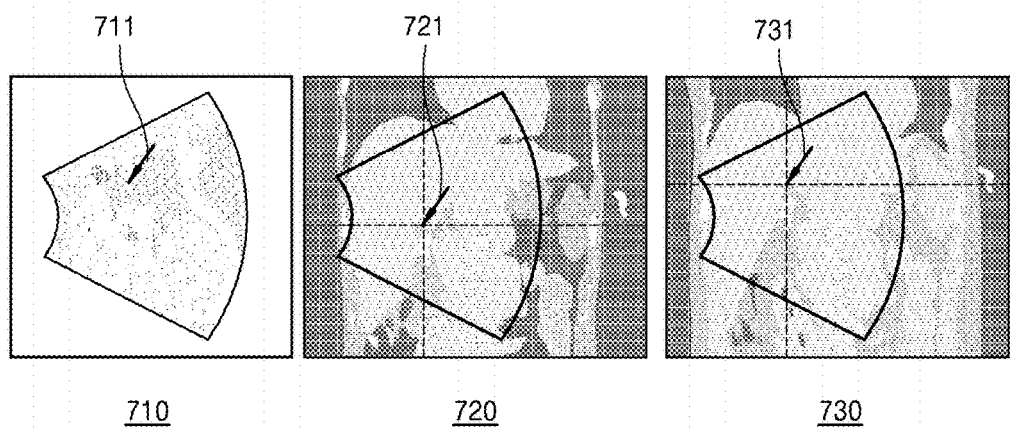
FIG. 7 is a diagram for explaining a matched image corresponding to a respiratory state, according to an exemplary embodiment.

FIG. 7 is a diagram for explaining a matched image corresponding to a respiratory state, according to an exemplary embodiment.

Referring to 710 of FIG. 7, an ultrasound image is acquired by scanning an object in an expiratory state. As shown in 710 of FIG. 7, a region of interest (ROI) or a position of interest) 711 is depicted in the ultrasound image for a doctor to treat or examine an affected area of a patient.

Referring to 720 of FIG. 7, the medical imaging apparatus 400 may match a CT image corresponding to an inspiratory state with the ultrasound image corresponding to the expiratory state and displays a matched image. A structural or spatial position of the object may vary depending on a respiratory state. As shown in 720 of FIG. 7, a position of an ROI 721 in the CT image corresponding to the inspiratory state does not coincide with a position of the ROI 711 in the ultrasound image corresponding to the expiratory state.

Furthermore, referring to 730 of FIG. 7, the medical imaging apparatus 400 may match a CT image corresponding to an expiratory state with the ultrasound image corresponding to the expiratory state and display a matched image. As shown in 730 of FIG. 7, a position of an ROI 731 in the CT image corresponding to the expiratory state coincides with the position of the ROI 711 in the ultrasound image corresponding to the expiratory state.

Thus, the medical imaging apparatus 400 may match a CT image and an ultrasound image corresponding to the same respiratory state and display a matched image. In this case, the respiratory state may be classified into two states, i.e., expiratory and inspiratory states. Furthermore, an inspiratory state may be divided into first through N-th inspiratory states depending on the degree to which the object inhales. Similarly, an expiratory state may be classified into first through N-th expiratory states according to the degree to which the object exhales.

Figure 8A:
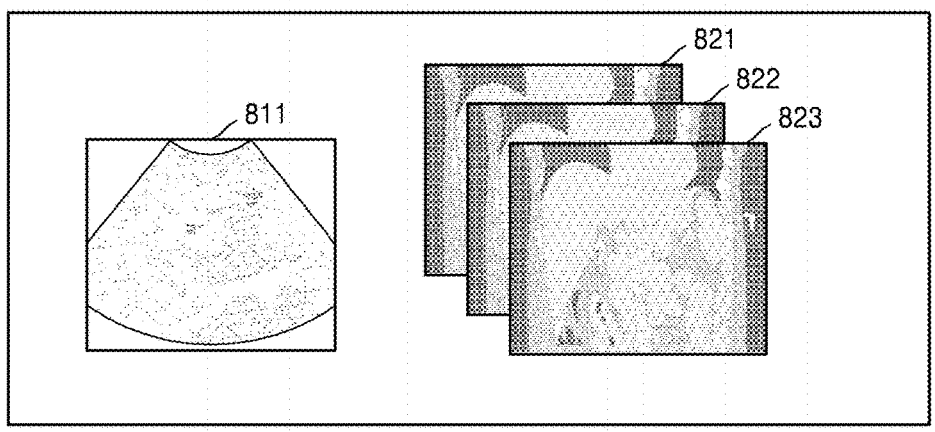
FIGS. 8A and 8B are diagrams for explaining an example where images of first and second types are displayed on a medical imaging apparatus, according to an exemplary embodiment.
Figure 8B:
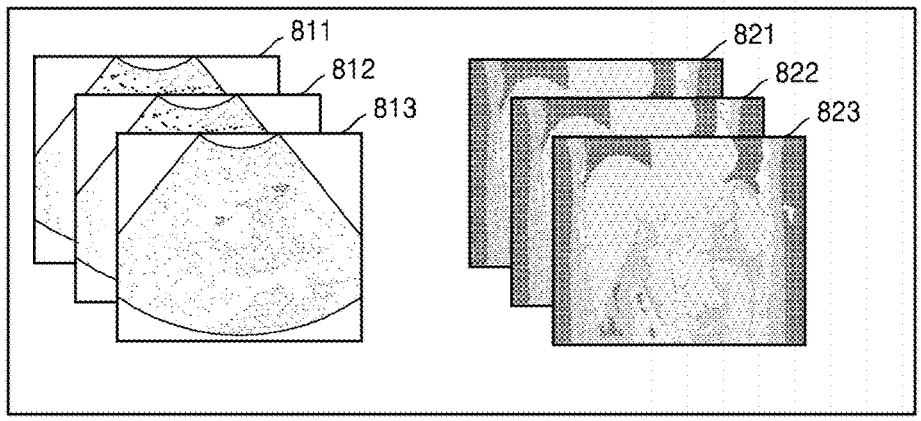

FIGS. 8A and 8B are diagrams for explaining an example where images of first and second types are displayed on the medical imaging apparatus 400, according to an exemplary embodiment.

The medical imaging apparatus 400 may display at least one of images of a first type and at least one of images of a second type.

Referring to FIG. 8A, the medical imaging apparatus 400 may display a first ultrasound image 811 of a second type and first through third CT images 821 through 823 of a first type. The first ultrasound image 811 of the second type and the first through third CT images 821 through 823 of the first type may be images depicting the same object and may correspond to different respiratory states of the object.

As shown in FIG. 8A, the medical imaging apparatus 400 may display the first ultrasound image 811 corresponding to a first respiratory state and the first through third CT images 821 through 823 corresponding to the first respiratory state. Furthermore, the medical imaging apparatus 400 may display the first through third CT images 821 through 823 in such a manner that they overlap one another or are separately arranged.

Referring to FIG. 8B, the medical imaging apparatus 400 may display first through third ultrasound images 811 through 813 of a second type and first through third CT images 821 through 823 of a first type.

As shown in FIG. 8B, the medical imaging apparatus 400 may display the first through third ultrasound images 811 through 813 corresponding to a first respiratory state and the first through third CT images 821 through 823 corresponding to the first respiratory state. Furthermore, the medical imaging apparatus 400 may display the first through third ultrasound images 811 through 813 in such a manner that they overlap one another or are separately arranged. Similarly, the medical imaging apparatus 400 may display the first through third CT images 821 through 823 in the overlapping or separate manner.

Figure 9A:
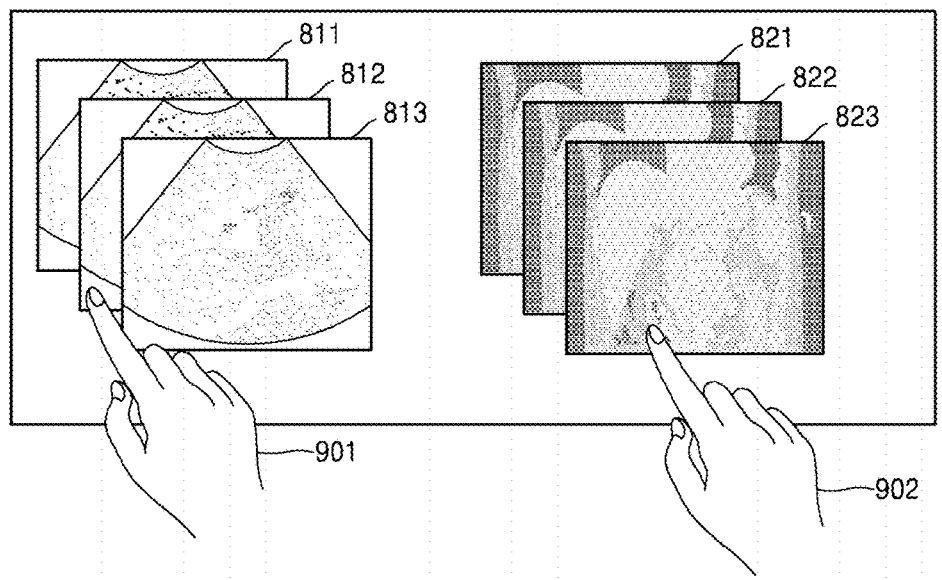
FIGS. 9A through 9C are diagrams illustrating diagrams illustrating results of performing registration on images selected by a user, according to an exemplary embodiment.
Figure 9B:
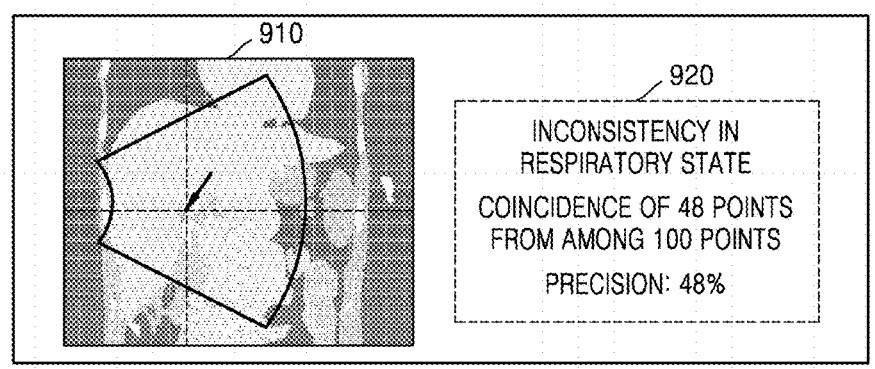
Figure 9C:
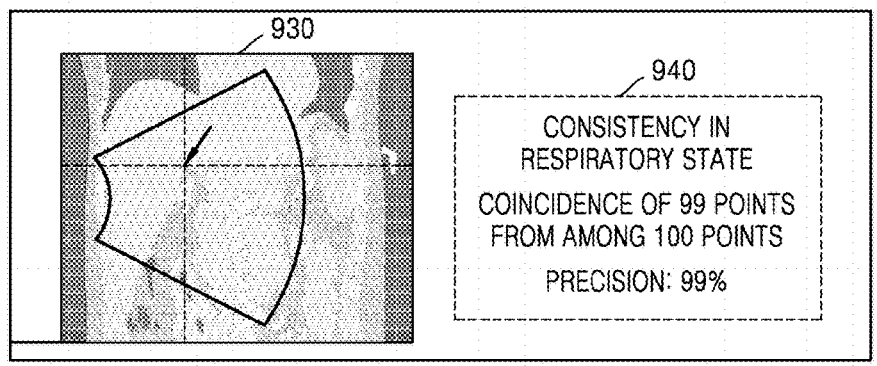

FIGS. 9A through 9C are diagrams illustrating results of performing registration on images selected by a user, according to an exemplary embodiment.

FIG. 9A illustrates selection of at least two of a plurality of images displayed on the medical imaging apparatus 400. As shown in FIG. 9A, the medical imaging apparatus 400 may display images 811 through 813 of a second type and images 821 through 823 of a first type. A user may select one from among the displayed images 821 through 823 of the first type as well as one from among the displayed images 811 through 813 of the second type.

As shown in FIG. 9A, when a screen of the medical imaging apparatus 400 is formed as a touch screen, the user uses a hand to select images of the first and second types. The medical imaging apparatus 400 may receive touch inputs 901 and 902 from the user and match images of the first and second types based on the received touch inputs 901 and 902.

Furthermore, although FIG. 9A shows that the medical imaging apparatus 400 receives a user input as a touch input, the medical imaging apparatus 400 may receive a user input via a user interface. In this case, the user interface may be a touch panel for sensing a touch input, and the touch panel may be integrated with the display 430) of the medical imaging apparatus 400.

Referring to FIGS. 9B and 9C, the medical imaging apparatus 400 may receive the touch inputs 901 and 902 as a user input and match one of the images of the first type with one of the images of the second type. The medical imaging apparatus 400 may display a matched image and resultant information of the matched image. The resultant information of the matched image may include pieces of information about whether respiratory states for two images coincide with each other, the number of main points in the two images that coincide with each other from among all main points of the object, and precision in registration between the two images. Furthermore, the medical imaging apparatus 400 may display precision by using an error in a position of one corresponding point between two images. The medical imaging apparatus 400 may determine whether the two images are acquired from the object in the same or different respiratory states, based on the error in a position of one corresponding point. One of ordinary skill in the art will understand that the resultant information of the matched image may include pieces of information other than those described above.

As shown in FIG. 9B, the medical imaging apparatus 400 may match a first image of a first type with a second image of a second type. In detail, the first image of the first type may be a CT image corresponding to an inspiratory state of the object, and the second image of the second type may be an ultrasound image corresponding to an expiratory state of the object. Since respiratory states for the first image of the first type and the second image of the second type are different from each other, positions of corresponding main points of the object in the first and second images may be different from each other. Thus, when the first and second images are matched together, precision in registration may be lower than that when images corresponding to the same respiratory state are matched. The medical imaging apparatus 400 may display "inconsistency in respiratory state", "coincidence of 48 points from among 100 points", and "precision of 48%" between the first and second images as the resultant information of a matched image.

As shown in FIG. 9C, the medical imaging apparatus 400 may match a second image of a first type with a second image of a second type. In detail, the second image of the first type may be a CT image corresponding to an expiratory state of an object, and the second image of the second type may be an ultrasound image corresponding to the expiratory state of the object. Since respiratory states for the second images of the first and second types are the same as each other, corresponding main points of the object in the second images of the first and second types may be located at the same position. Thus, when the second images of the first and second types are matched together, precision in registration may be higher than that when images corresponding to different respiratory states are matched. The medical imaging apparatus 400 may display "consistency in respiratory state", "coincidence of 99 points from among the entire 100 points", and "precision of 99%" between the second images of the first and second types as resultant information of a matched image.

The medical imaging) apparatuses described above may be implemented using hardware components, software components, or a combination thereof. For example, the apparatuses and components illustrated in the exemplary embodiments may be implemented using one or more general-purpose or special-purpose computers, such as a processor, a controller, an arithmetic logic unit (ALU), a digital signal processor, a microcomputer, a field programmable array (FPA), a programmable logic unit (PLU), a microprocessor or any other device capable of responding to and executing instructions in a defined manner.

A processing device may run an operating system (OS) and one or more software applications running on the OS. The processing device also may access, store, manipulate, process, and create data in response to execution of software.

For convenience, although a single processing device may be illustrated for convenience, one of ordinary skill in the art will appreciate that a processing device may include a plurality of processing elements and/or a plurality of types of processing elements. For example, a processing device may include a plurality of processors or a processor and a controller. In addition, the processing device may have different processing configurations such as parallel processors.

Software may include a computer program, a piece of code, an instruction, or one or more combinations thereof and independently or collectively instruct or configure the processing device to operate as desired.

Software and/or data may be embodied permanently or temporarily in any type of machine, component, physical equipment, virtual equipment, computer storage medium or device, or in a transmitted signal wave so as to be interpreted by the processing device or to provide instructions or data to the processing device. The software also may be distributed over network-coupled computer systems so that the software is stored and executed in a distributed fashion. In particular, the software and data may be stored in one or more computer-readable recording media.

The methods according to the exemplary embodiments may be recorded in non-transitory computer-readable recording media including program instructions to implement various operations embodied by a computer. The non-transitory computer-readable recording media may also include, alone or in combination with the program instructions, data files, data structures, and the like. The program instructions recorded in the non-transitory computer-readable recording media may be designed and configured specially for the exemplary embodiments or be known and available to those of ordinary skill in computer software.

Examples of non-transitory computer-readable recording media include magnetic media such as hard disks, floppy disks, and magnetic tape; optical media such as CD ROM discs and DVDs; magneto-optical media such as optical discs; and hardware devices that are specially configured to store and perform program instructions, such as ROM, RAM, flash memory, and the like.

Examples of program instructions include both machine code, such as that produced by a compiler, and higher level code that may be executed by the computer using an interpreter.

The above-described hardware devices may be configured to act as one or more software modules in order to perform the operations of the above-described embodiments, or vice versa.

While one or more exemplary embodiments have been described with reference to the figures, it will be understood by those of ordinary skill in the art that various modifications and changes in form and details may be made from the above descriptions without departing from the spirit and scope as defined by the following claims. For example, adequate effects may be achieved even if the above techniques are performed in a different order than described above, and/or the aforementioned elements, such as systems, structures, devices, or circuits, are combined or coupled in different forms and modes than as described above or are replaced or supplemented by other components or their equivalents.

Thus, the scope of the present inventive concept is defined not by the detailed description thereof but by the appended claims and their equivalents.

What is claimed is:

1. A method of operating a medical imaging apparatus, the method comprising:
    acquiring a first image of a first type corresponding to a first respiratory state of an object;
    acquiring a first image of a second type corresponding to the first respiratory state of the object and a second image of the second type corresponding to a second respiratory state of the object;
    determining a spatial transformation between the first image and the second image of the second type by using properties of anatomical structure extracted from the first image and the second image of the second type;
    determining motion information of the object with respect to a respiratory state, based on at least one parameter describing the spatial transformation between the first image and the second image of the second type; and
    generating a second image of the first type corresponding to the second respiratory state by applying the motion information to the first image of the first type; and
    registering one of the first and the second images of the first type and one of the first and the second images of the second type,
    wherein the registered one of the first and the second images of the first type and the registered one of the first and the second images of the second type are both of the first respiratory state or the second respiratory state, and
    wherein anatomical structures and position information of the object in the registered one of the first and the second images of the first type and anatomical structures and position information of the object in the registered one of the first and the second images of the second type, coincide with each other.

2. The method of claim 1, wherein the registering comprises registering the first image of the first type corresponding to the first respiratory state with the first image of the second type corresponding to the first respiratory state; and
    wherein the registering comprises registering the second image of the first type corresponding to the second respiratory state with the second image of the second type corresponding to the second respiratory state.

3. The method of claim 1, further comprising displaying a registered image.

4. The method of claim 1, further comprising:
    displaying at least one of the first and second images of the first type and at least one of the first and second images of the second type; and
    receiving a user input for selecting the at least one of the first and second images of the first type and the at least one of the first and second images of the second type.

5. The method of claim 4, further comprising registering the selected at least one image of the first type with the selected at least one image of the second type.

6. The method of claim 4, wherein the displaying of the at least one of the first and second images of the first type and the at least one of the first and second images of the second type comprises at least one of:
    displaying the first and second images of the first type and the first and second images of the second type; and
    displaying at least two of the first and second images of the first type and the first and second images of the second type in such a manner that the at least two images overlap each other.

7. The method of claim 6, wherein the displaying of the at least two of the first and second images of the first type and the first and second images of the second type in the overlapping manner comprises at least one of:
    displaying the first and second images of the first type in the overlapping manner; and
    displaying the first and second images of the second type in the overlapping manner.

8. The method of claim 1, wherein the determining of the motion information of the object with respect to the respiratory state comprises:
    determining the at least one parameter for acquiring motion information indicating the spatial transformation between the first and second images of the second type;
    determining a value of the at least one parameter based on the spatial transformation therebetween; and
    determining the motion information based on the determined value of the at least one parameter.

9. The method of claim 8, wherein the spatial transformation is based on at least one of a position, rotation, and a size of the object.

10. The method of claim 1, wherein the determining of the motion information of the object with respect to the respiratory state comprises acquiring position information of the object and determining the motion information from the first and second images of the second type respectively acquired in the first and second respiratory states corresponding to the acquired position information.

11. The method of claim 1, wherein the first and second images of the first type are computed tomography (CT) images, and the first and second images of the second type are ultrasound images.

12. The method of claim 1, wherein the first and second respiratory states are inspiratory and expiratory states of the object, respectively.

13. A medical imaging apparatus comprising:
    an image processor configured to acquire a first image of a first type corresponding to a first respiratory state of an object, and to acquire a first image of a second type corresponding to the first respiratory state of the object and a second image of the second type corresponding to a second respiratory state of the object;
    a controller configured to determine motion information of the object with respect to a respiratory state based on at least one parameter describing spatial transformation between the first image and the second image of the second type, and to generate a second image of the first type corresponding to the second respiratory state by applying the motion information to the first image of the first type, and to register one of the first and the second images of the first type and one of the first and the second images of the second type, wherein the registered one of the first and the second images of the first type and the registered one of the first and the second images of the second type are both of the first respiratory state or the second respiratory state, and wherein anatomical structures and position information of the object in the registered one of the first and the second images of the first type and anatomical structures and position information of the object in the registered one of the first and the second images of the second type, coincide with each other.

14. The medical imaging apparatus of claim 13, wherein the controller registers the first image of the first type corresponding to the first respiratory state with the first image of the second type corresponding to the first respiratory state, and registers the second image of the first type corresponding to the second respiratory state with the second image of the second type corresponding to the second respiratory state.

15. The medical imaging apparatus of claim 13, further comprising:
  a display configured to display at least one of the first and second images of the first type and at least one of the first and second images of the second type; and
  a user interface configured to receive a user input for selecting the at least one of the first and second images of the first type and the at least one of the first and second images of the second type.

16. The medical imaging apparatus of claim 15, wherein the display displays at least two of the first and second images of the first type and the first and second images of the second type in such a manner that the at least two images overlap each other.

17. The medical imaging apparatus of claim 13,
  wherein the controller determines the at least one parameter for acquiring motion information indicating the spatial transformation between the first and second images of the second type, determines a value of the at least one parameter based on the spatial transformation therebetween, and determines the motion information based on the determined value of the at least one parameter.

18. A non-transitory computer-readable recording medium having recorded thereon a program for performing a method of operating a medical imaging apparatus, wherein the method comprises:
  acquiring a first image of a first type corresponding to a first respiratory state of an object;
  acquiring a first image of a second type corresponding to the first respiratory state of the object and a second image of the second type corresponding to a second respiratory state of the object;
  determining a spatial transformation between the first image and the second image of the second type by using properties of anatomical structure extracted from the first image and the second image of the second type;
  determining motion information of the object with respect to a respiratory state, based on at least one parameter describing the spatial transformation between the first image and the second image of a second type; and generating a second image of the first type corresponding to the second respiratory state by applying the motion information to the first image of the first type; and
registering one of the first and the second images of the first type and one of the first and the second images of the second type,
wherein the registered one of the first and the second images of the first type and the registered one of the first and the second images of the second type are both of the first respiratory state or the second respiratory state, and
wherein anatomical structures and position information of the object in the registered one of the first and the second images of the first type and anatomical structures and position information of the object in the registered one of the first and the second images of the second type, coincide with each other.

19. A method of operating a medical imaging apparatus, the method comprising:
  acquiring a first image of a first type corresponding to a first respiratory state of an object and images of a second type respectively corresponding to a plurality of respiratory states;
  acquiring position information of the object indicating a spatial transformation between the images of the second type by using properties of anatomical structure extracted from the images of the second type;
  determining motion information of the object with respect to a respiratory state, based on the acquired position information of the object and the images of the second type; and
  generating a second image of the first type corresponding to a second respiratory state by applying the motion information to the first image of the first type; and
  registering one of the first and the second images of the first type and one of the first and the second images of the second type,
  wherein the registered one of the first and the second images of the first type and the registered one of the first and the second images of the second type are both of the first respiratory state or the second respiratory state, and
  wherein anatomical structures and position information of the object in the registered one of the first and the second images of the first type and anatomical structures and position information of the object in the registered one of the first and the second images of the second type, coincide with each other.

20. The method of claim 19, further comprising:
displaying a registered image.

21. The method of claim 19, wherein the determining of the motion information with respect to the respiratory state comprises determining the motion information based on the position information of the object and the anatomical structures in the images of the second type.

22. A medical imaging apparatus comprising:
  an image processor configured to acquire a first image of a first type corresponding to a first respiratory state of an object and images of a second type respectively corresponding to a plurality of respiratory states; and
  a controller configured to acquire position information of the object indicating a spatial transformation between the images of the second type by using properties of anatomical structure extracted from the images of the second type, determine motion information of the object with respect to a respiratory state, based on the acquired position information of the object and the images of the second type, and generate a second image of the first type corresponding to a second respiratory state by applying the motion information to the first image of the first type, and to register one of the first and the second images of the first type and one of the first and the second images of the second type, wherein the registered one of the first and the second images of the first type and the registered one of the first and the second images of the second type are both of the first respiratory state or the second respiratory state, and wherein anatomical structures and position information of the object in the registered one of the first and the second images of the first type and anatomical structures and position information of the object in the registered one of the first and the second images of the second type, coincide with each other.

23. The medical imaging apparatus of claim 22, further comprising a display configured to display a registered image.

* * * * *